(12) United States Patent
Vadlamudi et al.

(10) Patent No.: US 9,278,224 B1
(45) Date of Patent: Mar. 8, 2016

(54) ELECTRICAL CONNECTOR RING FOR IMPLANTABLE MEDICAL DEVICE

(71) Applicant: DONATELLE PLASTICS, INC., New Brighton, MN (US)

(72) Inventors: Raghu Vadlamudi, Woodbury, MN (US); Matthew L. Iwen, Savage, MN (US); Clint J. Fonder, Elk River, MN (US)

(73) Assignee: Donatelle Plastics, Inc., New Brighton, MN (US)

( * ) Notice: Subject to any disclaimer, the term of this patent is extended or adjusted under 35 U.S.C. 154(b) by 0 days.

(21) Appl. No.: 14/531,077

(22) Filed: Nov. 3, 2014

(51) Int. Cl.
*A61N 1/00* (2006.01)
*A61N 1/375* (2006.01)

(52) U.S. Cl.
CPC .................................. *A61N 1/3752* (2013.01)

(58) Field of Classification Search
CPC ........................... A61N 1/3752; A61N 1/3754
See application file for complete search history.

(56) References Cited

U.S. PATENT DOCUMENTS

| | | | |
|---|---|---|---|
| 4,934,367 A | 6/1990 | Daglow et al. | |
| 6,895,276 B2 | 5/2005 | Kast et al. | |
| 7,003,351 B2 | 2/2006 | Tvaska et al. | |
| 7,587,244 B2 | 9/2009 | Olbertz | |
| 8,666,494 B2 | 3/2014 | Schramm et al. | |
| 2011/0104955 A1* | 5/2011 | Seeley et al. | 439/668 |
| 2012/0232603 A1* | 9/2012 | Sage | A61N 1/3752 607/2 |

\* cited by examiner

*Primary Examiner* — Scott Getzow
(74) *Attorney, Agent, or Firm* — Nikolai & Mersereau, P.A.; Thomas J. Nikolai

(57) ABSTRACT

A multi-foil ringlet in combination with a cylindrical housing provides advantageous results when employed as a contact of a header of an implantable pulse generator. The multi-foil ringlet provides a superior electrical connection between the header and a lead pin inserted into the header.

14 Claims, 4 Drawing Sheets

ELECTRICAL CONNECTOR RING FOR IMPLANTABLE MEDICAL DEVICE

CROSS-REFERENCED TO RELATED APPLICATIONS

Not applicable.

STATEMENT REGARDING FEDERALLY SPONSORED RESEARCH OR DEVELOPMENT

Not applicable.

BACKGROUND OF THE INVENTION

I. Field of the Invention

The present invention relates to implantable pulse generators and, more particularly, implantable pulse generator headers and the electrical connectors used in the construction of such headers. The present invention also relates to methods for manufacturing electrical connectors for headers for implantable pulse generators.

II. Discussion of Related Art

In medical technology an implanted pulse generator (IPG) may be employed for a variety of purposes. An IPG is a battery powered device designed to deliver electrical stimulation to the body. An IPG is typically an integral component of a surgically implanted system, which includes the IPG, one or more leads and an external programmer. Such systems fall into two broad categories, neuromodulation systems and cardiac rhythm management systems. Neuromodulation systems are used, for example, to provide deep brain stimulation, vagus nerve stimulation, spinal cord stimulation, peripheral nerve stimulation and the like. Such stimulation has proven to be beneficial for the treatment of intractable pain, Parkinson's disease, pelvic disorders and incontinence, sleep apnea, and epilepsy, among other conditions. Cardiac rhythm management systems include heart pacemakers, defibrillators, cardioverters and other forms of devices used to monitor and control heart rhythms.

The IPG is typically implanted within a person's body, usually beneath the clavicle. Leads are then routed through the body between the site to be stimulated and the IPG. The leads are then coupled to the header of the IPG to carry signals between the IPG and the treatment site. The IPG can be calibrated using the external programmer by a physician (such as an electrophysiologist, neurologist or cardiologist) or by a nurse or other trained technician to meet the individual patient's needs. The IPG must be replaced periodically upon battery depletion. Battery depletion can occur within three to five years, though battery life is dependent on individual usage. End of battery life can be reasonably predicted by the use of telemetry between the IPG and the external programming device. This allows the IPG to be replaced prior to battery failure.

As indicated above, one example of an IPG is a heart pacemaker (or artificial heart pacemaker, so as not to be confused with the heart's natural pacemaker), a medical device which uses electrical impulses to regulate the beating of the heart. When the IPG is employed as an artificial heart pacemaker, the IPG is used in combination with a lead comprising a set of electrodes which carry stimulation pulses from the IPG to the heart and electrical signals back from the heart to the IPG which senses and responds to such signals. The primary purpose of a pacemaker is to maintain an adequate heart rate, either because the heart's native pacemaker is not fast enough, or because there is a block in the heart's electrical conduction system. Modern pacemakers are externally programmable and allow the electrophysiologist to select the optimum pacing modes for individual patients. Some IPG devices combine a pacemaker and defibrillator in a single implantable device. Multiple electrodes stimulating differing positions within the heart are often used to improve synchronization of the contractions of the upper and lower and chambers of the heart.

Another type of IPG is an implantable cardioverter-defibrillator (ICD), a small battery-powered electrical pulse generator which is implanted in patients who are at risk of sudden death due to ventricular fibrillation or ventricular tachycardia. The device is programmed to detect cardiac arrhythmia and correct it by delivering a jolt of electricity. In current variants, ICD devices have the ability to treat both atrial and ventricular arrhythmias as well as the ability to perform biventricular pacing in patients with congestive heart failure or bradycardia.

The process of implantation of an ICD is similar to implantation of a pacemaker. Like pacemakers, ICD devices are coupled to a set of leads containing electrode(s) and wire(s) which are passed though the vasculature to desired locations in the heart. For example an electrode can be passed through a vein to the right chambers of the heart, and then lodged in the apex of the right ventricle. Providing defibrillation pulses at this location has been found to be advantageous. As is the case with pacemaker leads, the leads are coupled to the header of the ICD and used to carry both stimulation pulses from the ICD to the heart and electrical signals from the heart to the ICD.

ICDs constantly monitor the rate and rhythm of the heart and can deliver therapies, by way of an electrical shock, when the electrical manifestations of the heart activity exceed one or more preset thresholds. More modern devices can distinguish between ventricular fibrillation and ventricular tachycardia (VT) and may try to pace the heart faster than its intrinsic rate in the case of VT, to try to break the tachycardia before it progresses to ventricular fibrillation. This is known as fast-pacing, overdrive pacing or anti-tachycardia pacing (ATP). ATP is only effective if the underlying rhythm is ventricular tachycardia, and is never effective if the rhythm is ventricular fibrillation.

Other IPG devices serve as neurostimulators and are used to treat pain, incontinence, and other neurologic and muscular conditions. Such IPG devices have a header used to couple the IPG to leads containing a plurality of wires and electrodes which deliver stimulating pulses from the IPG to nerves and muscles to provide beneficial therapies. The electrodes and wires of the leads may also be used to carry electrical signals back to the IPG.

The various types of IPG devices referenced above typically have a header to which the leads are attached. The header typically includes one or more bores each configured to receive a terminal pin of a lead. The terminal pin will typically contain a plurality of electrodes spaced along its length. Likewise, the bore will typically have a matching set of electrical contacts along its length which are spaced to form electrical connections with the electrodes of the lead pin. The electrical connections should be isolated from each other to prevent a short or unintended propagation of signals along a particular channel. The number and spacing or the electrodes and contacts may vary, but standards have emerged related to such numbers and such spacing for various types of stimulation systems.

Various types of electrical contacts have been employed in the headers of IPG devices. Prior art header designs often employed thin wire connections, female leaf springs, canted coil springs or "slide by" wire connectors. Many of these provided adequate electrical connection, but were fragile in design. Such connectors were easily damaged during pin insertion or incapable of producing mechanical forces sufficient to hold the pin in the desired orientation.

U.S. Pat. No. 4,934,367 granted to Daglow et al on Jun. 19, 1990 discloses the use of elastomeric rings either made of a conductive polymer or a non-conductive polymer impregnated with a conductive material. This and other patents also disclose the use of springs. For example, U.S. Pat. No. 6,895,276 granted to Kast et al on May 17, 2005 discloses a contact comprising a cylindrical housing comprising a wall having an inner surface defining a bore, a channel between the inner surface of the wall and the bore and a continuous spring fitted within the channel. U.S. Pat. No. 7,003,351 granted to Tvaska et al on Feb. 21, 2006 and U.S. Pat. No. 7,587,244 granted to Olbertz on Sep. 8, 2009 each show a connector with a similar ring having a plurality of spring contact members attached thereto. Further, U.S. Pat. No. 8,666,494 granted to Schramm et al discloses a spring contact ring comprising a housing including a recess channel and a spring comprising a base and a plurality of spring fingers.

Designing a connector for use in the header of an IPG device presents a variety of challenges which arise from the difficulty in maintaining the desired balance between mechanical and electrical properties. Examples of such challenges include: (1) limiting the mechanical insertion force required to insert the lead pin because excessive pressure exerted on the inner seal and electrical components of the bore can result in damage to the header; (2) excessive electrical engagement between the contacts of the header and the lead pin can result in shorts or faults which can draw off potential battery power; (3) insufficient mechanical retention forces can result in an electrode of the bore losing position or falling out of place; and (4) maintaining proper manufacturing tolerances. The tolerances of the electrode lead wires present further challenges with respect to the header's ability to achieve the desired electrical and mechanical responses. Thus, there continues to exist a real and substantial need to provide efficient and cost effective manufacturing methods and electrical contact designs for headers which meet these challenges.

SUMMARY OF THE INVENTION

The aforementioned problems are solved by providing a ringlet coupler which can be employed in the header of an implantable pulse generator and which is adapted to make an electrical connection with a contact of a lead pin of a medical lead. The components of the ringlet coupler can be inexpensively and quickly fabricated using high speed machining operations. Only a few assembly steps are required.

The components include a housing having a wall defining an inner surface and an outer surface. The components also include an electrically conductive ringlet. The band also has an inner surface and an outer surface and is fabricated into a pattern consisting of at least three smoothly curved foils joined together by smoothly curved reduced diameter sections between each adjacent pairs of foils. The reduced diameter sections define a channel and the foils are equally spaced about this channel. When the ringlet is placed in the housing, the apex of each foil is in contact with the inner surface of the housing. When a lead pin is inserted into the channel, the reduced diameter sections simultaneously engage the lead pin to form an electrical connection. Likewise, the reduced diameter sections cooperate with the foils and the housing to mechanically secure the lead pin to the electrically conductive ringlet. One or more supports may be employed to secure the ringlet to the inner surface of the housing.

Electrical contact and the mechanical holding force of the ringlet are typically improved by providing a concave area of reduced thickness at each of the reduced diameter sections. These concave areas extend inwardly from the second inner surface of the band. Similar concave areas of reduced thickness may be provided at the apex of the foils. These reduced diameter sections serve other important functions as well. They permit flexing of the ringlet which assists with assembly of the ringlet and the housing. Such flexing is also advantageous to permit insertion and withdrawal of the lead pin. Such flexing is further assisted by providing a break at the apex of one of the foils.

The housing and the ringlet can be made from a wide variety of materials. Conductive alloys suitable for use when forming the ringlet include a nickel, cobalt, chromium and molybdenum alloy made in conformance with ASTM F562-13 which is widely used for surgical implants. This alloy is known for its strength and ductility. Other suitable materials include conductive thermoplastics, combinations of thermoplastics and metals, and other metals such as platinum-iridium, iron, titanium, gold, silver, copper and various conductive alloys.

The number of foils of the ringlet can be increased beyond three. In addition to a trefoil shape, other shapes (such as a quatrefoil shape, a pentafoil shape or a hexafoil shape) may be employed.

Assembly of the ringlet to the housing can occur in several different ways. For example, the ringlet may be inserted through one of the two open ends of the housing. Alternatively, a slot may be provided through the wall of the housing and the ringlet can then be inserted through this slot.

Various supports may be employed to secure the ringlet in place to the inner surface of the housing. For example, a recessed channel defined by a pair of walls extending from the inner surface of the ring may be employed. The ringlet may be positioned in this channel such that the two channel walls extend on opposite sides of the ringlet. Alternate supports may be employed to couple the ringlet in place with the housing. The housing may also have an internal wall which prevents the ringlet from being pushed all the way through the housing. A cap may also be employed such that the ringlet is sandwiched between the internal wall and cap within the housing.

DESCRIPTION OF PREFERRED EMBODIMENT

Figure 1:
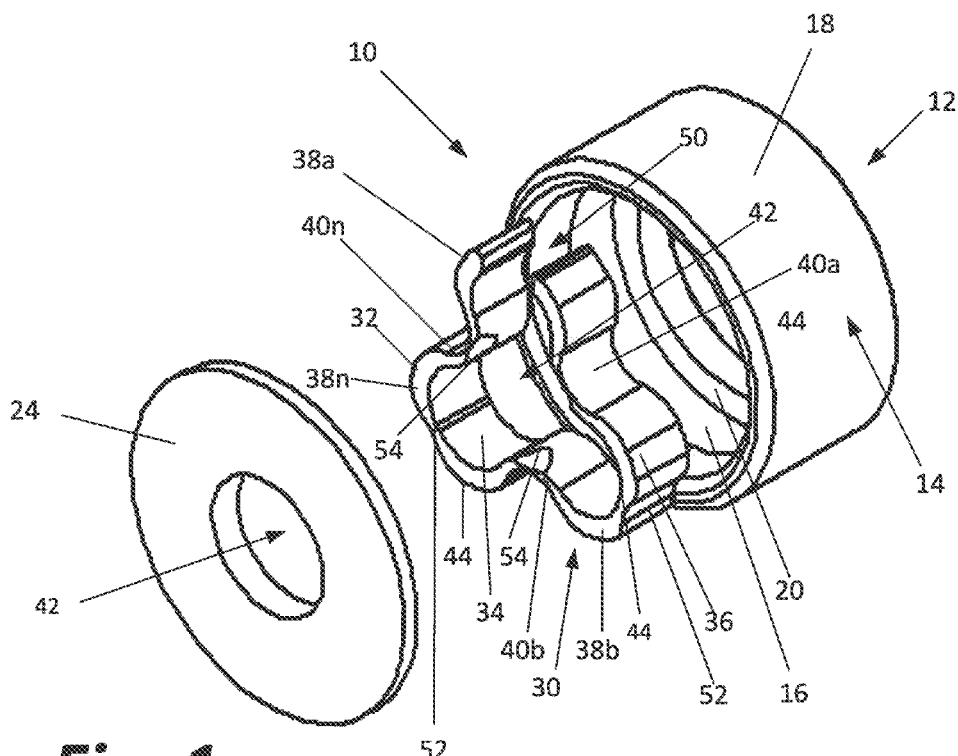
FIG. 1 is a perspective exploded view of a ringlet coupler wherein the ringlet has a trefoil shape.

The following discussion is presented to enable a person skilled in the art to make and use the present teachings. Various modifications to the illustrated embodiments will be readily apparent to those skilled in the art, and the principles described herein may be applied to other embodiments and applications without departing from the present invention. Thus, the present invention is not intended to be limited to embodiments shown, but is to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the present invention. Skilled artisans will recognize many useful alternatives to the teachings and the examples provided herein falling within the scope of the invention exist and may be employed without deviating from the invention.

FIG. 1 shows a ringlet coupler 10 comprising a housing 12 and a ringlet 30. The housing 12 has an outer cylindrical wall 14 with a first inner surface 16 and a first outer surface 18. Extending inwardly from the first inner surface 16 is a support or wall 20. The support 20 provides a seat against which the ringlet 30 rests to prevent the ringlet 30 from being pushed all the way through the housing 12. In this fashion, the wall 20 is a support adapted to secure the ringlet 30 to the inner surface 16 of the housing. The housing 12 also includes a cap 24. After the ringlet 30 is inserted into the housing, cap 24 is then inserted and fastened in place using a weld, adhesive or friction such that the ringlet is sandwiched between and supported between the cap 24 and wall 20, further securing the ringlet 30 to the inner surface 16 of the housing 12.

Figure 3:
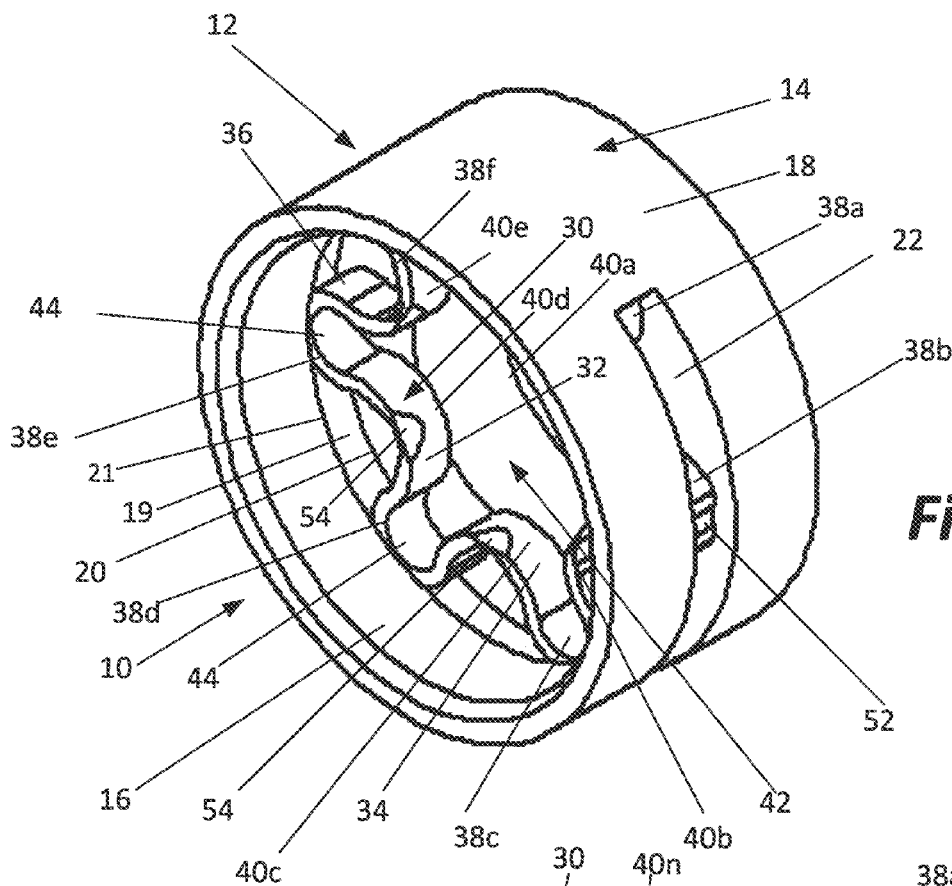
FIG. 3 is a perspective view of an alternative embodiment of a ringlet coupler wherein the ringlet has a hexafoil shape.

Various alterations may be made to the housing. As shown in FIG. 3, the cylindrical wall 14 may be provided with a slot 22 through which the ringlet 30 may be inserted into the housing 12. As is also shown in FIG. 3, rather than the housing 30 having a wall 20 and cap 24, the housing 30 may be provided with a channel 19 defined by walls 20 and 21. The channel 19 is aligned with slot 22 so that the ringlet 30 may be inserted through slot 22 and into the channel 19 to capture the ringlet 30 in the channel 19 between walls 20 and 21 which serve as a support to secure the ringlet 30 to the inner surface 16 of the housing.

Figure 2:
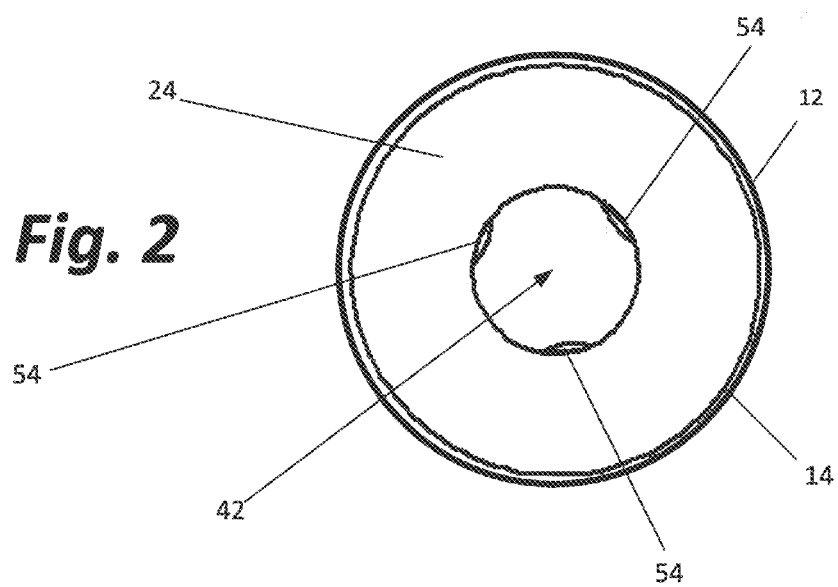
FIG. 2 is an end view of the ringlet coupler of FIG. 1.
Figure 5:
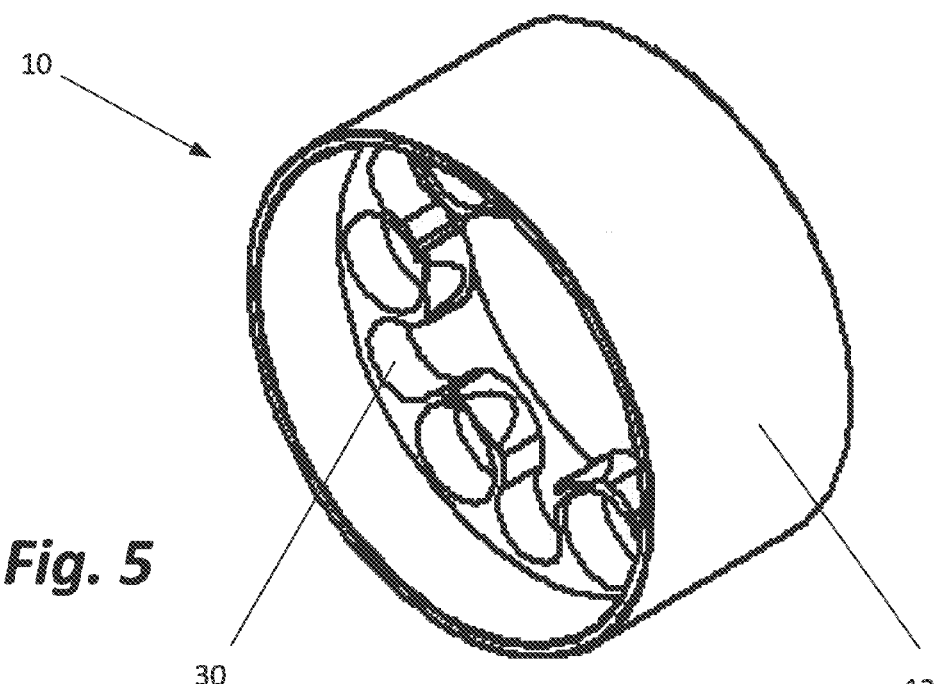
FIG. 5 is a perspective view of an alternative embodiment of a ringlet coupler having a hexafoil shape.
Figure 6:
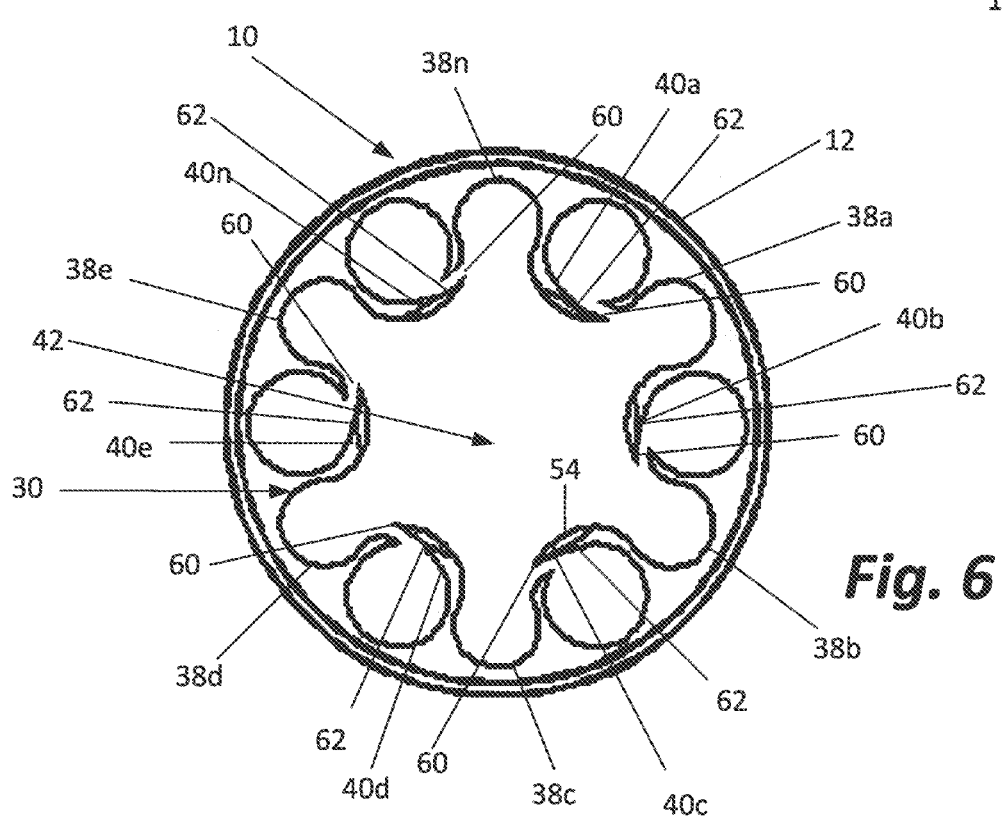
FIG. 6 is an end view of the ringlet coupler of FIG. 5.
Figure 7:
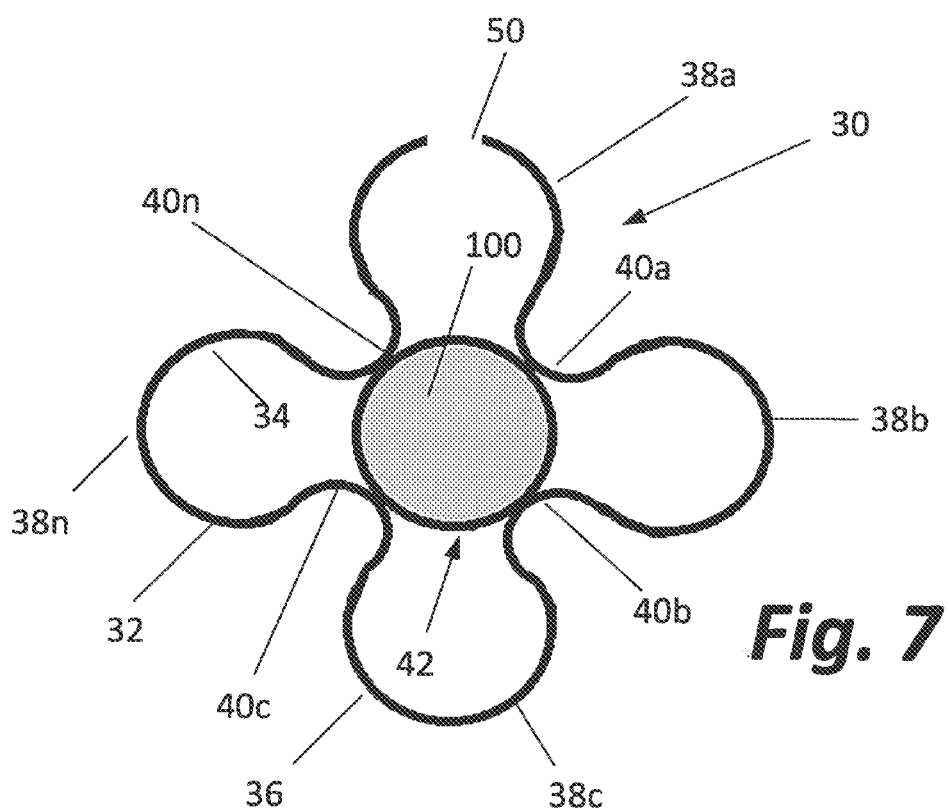
FIG. 7 is a plan view of a quatrefoil shaped ringlet.
Figure 8:
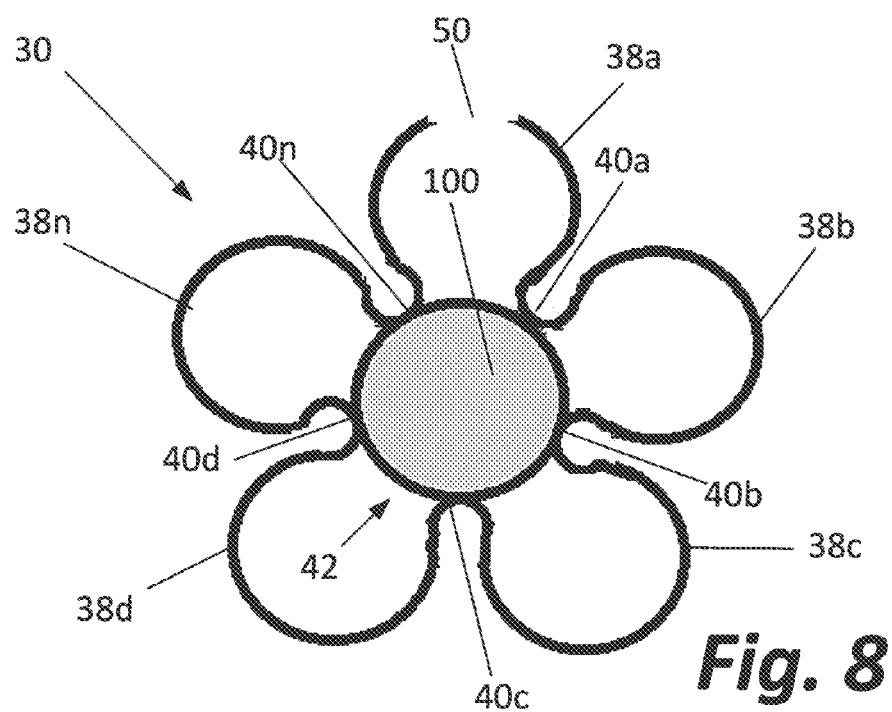
FIG. 8 is a plan view of a pentafoil shaped ringlet.

FIGS. 1-8 show alternative ringlets 30. In each embodiment, the ringlets 30 comprise a band 32. The band 32 has a second inner surface 34 and a second outer surface 36. The band is fabricated into smoothly curved foils 38a-n. The foils 38a-n are joined together by smoothly curved reduced diameter sections 40a-n. FIGS. 1 and 2 show a ringlet 30 as having a trefoil configuration while FIGS. 3-6 show a ringlet 30 having a hexafoil configuration. FIG. 7 shows the ringlet 30 having a quatrefoil configuration and FIG. 8 shows the ringlet having a pentafoil configuration. The number of foils is not critical so long as at least three foils are present.

Irrespective of the number of foils, 38a-n, they are preferably equally spaced about a channel 42 defined by the reduced diameter sections 40a-n. Channel 42 extends not only through the ringlet 30, but also through the housing 12 and any cap 24 which is employed. A lead pin 100 is inserted into the channel 42 to couple the lead to the ringlet coupler 10.

Each foil 38a-n has an apex 44. When assembled, the apex 44 of each foil 38a-n is adjacent to and typically is in contact with the inner surface 16 of the housing 12. When a pin 100 of a medical lead (shown in FIGS. 7 and 8) is inserted into the channel 42, the reduced diameter sections 40a-n simultaneously engage the lead pin 100 to form an electrical connection between the ringlet coupler 10 and the lead pin 100. Further, the reduced diameter sections 40a-n cooperate with the foils 38a-n and the housing 12 to mechanically secure the lead pin 100 to the ringlet 30.

The ringlet 30 is made of an electrically conductive material. The housing 12 may also be made of an electrically conductive material. If the housing 12 is electrically conductive, wires (not shown) extending to the circuitry of the pulse generator are coupled to the housing 12. Otherwise, such wires are coupled to the ringlet 30. The ringlet 30 may be made of any suitable conductive, biocompatible material. Alloys of cobalt, nickel, chromium and molybdenum made in conformance with ASTM International Standard F562-13 have proven to be well suited for use in medical implants generally. Such an alloy is also well suited for forming the ringlet 30. As discussed above, various thermoplastics, combinations of thermoplastics and metals, metals, and metal alloys may be used to fabricate the ringlet 30.

Irrespective of the number of foils, the ringlet 30 may also be provided with other desirable features. As shown in FIGS. 1, 7 and 8, the ringlet 30 includes a break 50. This break 50 enhances flexibility of the ringlet 30 which aid in insertion of the ringlet into the housing. This break 50 also allows the ringlet 30 to flex (without damage to the lead or ringlet coupler 10) as a lead pin is pushed into or pulled out of the channel 42. To further aid such flexibility and provide better attachment between the ringlet 30 and the cylindrical wall of the housing 12, the apex 44 of each foil 38a-n (other than the foil including the break 50) may be provided with a concave area 52 of reduced thickness extending inwardly from the second outer surface 36. To still further aid in providing such flexibility and increase the area of contact between the ringlet 30 and the lead pin 100, a concave area 54 of reduced thickness extending inwardly from the second inner surface 34 may be provided at each of the reduced diameter sections 40a-n.

Figure 4:
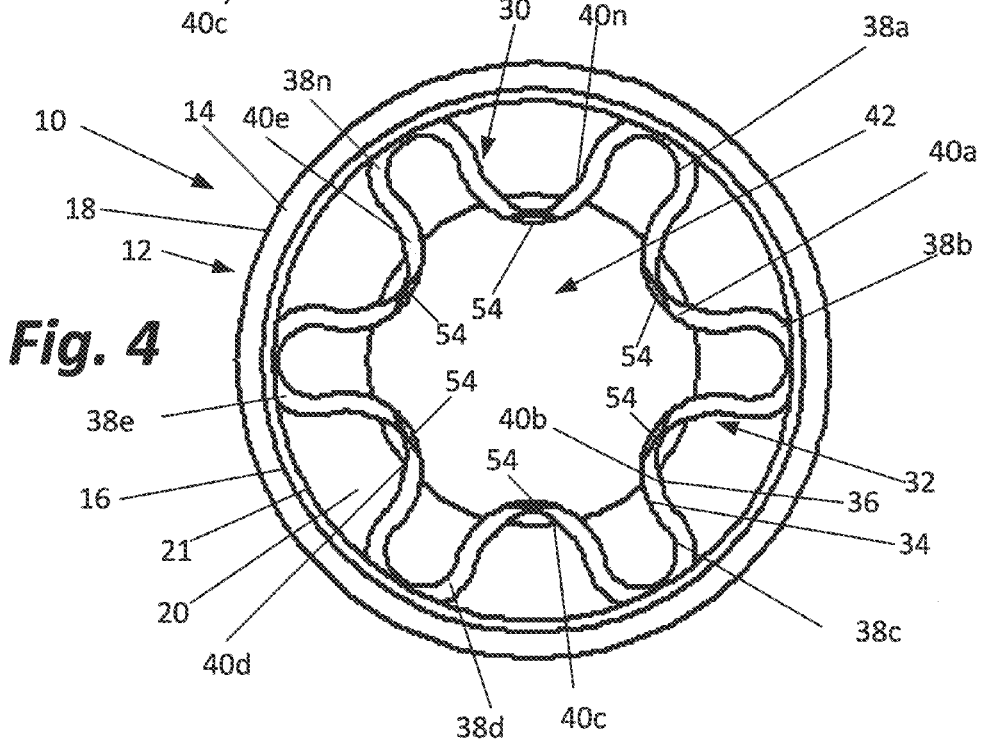
FIG. 4 is an end view of the ringlet coupler of FIG. 3.

The embodiment of FIGS. 1 and 2 and the embodiment of FIGS. 3 and 4 each show a separately fabricated housing 12 and ringlet 30 which are coupled together. It is, however, possible to fabricate the housing 12 and ringlet 30 as a single piece. FIGS. 5 and 6 show such an embodiment. Specifically, housing 12 and ringlet 30 of the ringlet coupler 10, shown in FIGS. 5 and 6, are fabricated as a single piece, either as part of a cutting, molding or other fabrication process. This eliminates the need for the support wall 20 and cap 24 of the embodiment of FIGS. 1 and 2 or the need for the slot 22 and channel 19 defined by walls 20 and 21 in the embodiment of FIGS. 3 and 4.

Further, while the embodiment shown in FIGS. 5 and 6 has a hexafoil-shaped ringlet 30 like the embodiment shown in FIGS. 3 and 4, the reduced diameter sections 40a-n of the embodiment of FIGS. 5 and 6 differ because they each include a small gap 60 and a flap 62 which at least partially closes the gap 60 when a pin 100 is inserted into the channel 42. As such, the pin is resiliently engaged by the flaps 62.

As noted above, while FIGS. 1 and 2 show trefoil shaped ringlet 30 and FIGS. 3-6 show a hexafoil-shaped ringlet 30, other shapes may be employed such as the quatrefoil shape shown in FIG. 7 and the pentafoil shape shown in FIG. 8. To achieve proper electrical and mechanical contact with the lead pin 100, there must be at least three foils. Any reasonable number of additional foils may be employed.

Those skilled in the art will recognize that a plurality of the ringlet couplers 10 may be stacked with seals (not shown) separating the electrical connectors. Stacks of connectors 10 and seals may then be overmolded with silicone or some other suitable material to form the header of a pulse generator. See, for example, U.S. Pat. No. 8,666,494 to Schramm et al, granted Mar. 4, 2014, which is incorporated by reference and shows a stack of electrical connectors and seals overmolded to form the header of an implantable pulse generator. The lead pin 100 is used to couple the lead to the pulse generator.

The foregoing discussion of various embodiments of the invention is not intended to be limiting. They are instead intended to describe the invention in sufficient detail to enable one of ordinary skill in the art. The scope of the invention is only limited by the following claims.

What is claimed is:

1. A ringlet coupler employed in the header of an implantable pulse generator and adapted to make an electrical connection with a contact of a lead pin of a medical lead, said ringlet coupler comprising:
   (a) an electrical conductive housing comprising an outer cylindrical wall defining a first inner surface and a first outer surface with a pair of cylindrical walls extending inwardly from the first inner surface of the outer cylindrical wall of the housing;
   (b) an electrically conductive ringlet comprising a band having a second inner surface and a second outer surface, said band fabricated into at least three smoothly curved foils joined together by smoothly curved reduced diameter sections between adjacent foils, wherein said foils are equally spaced about a channel defined by said reduced diameter sections, wherein each foil has an apex adjacent to the inner surface of the housing, wherein the reduced diameter sections are adapted to simultaneously engage a lead pin inserted into the channel to form an electrical connection and cooperate with the foils and the housing to mechanically secure such a lead pin to the electrically conductive ringlet; and
   (c) means for securing the ringlet to the housing.

2. The ringlet coupler of claim 1 wherein said band further comprises a concave area of reduced thickness at each of the reduced diameter sections extending inwardly from the second inner surface.

3. The ringlet coupler of claim 1 wherein said ringlet is made of a conductive alloy.

4. The ringlet coupler of claim 3 wherein said metal alloy comprising nickel, cobalt, chromium and molybdenum.

5. The ringlet coupler of claim 1 wherein said ringlet has a trefoil shape.

6. The ringlet coupler of claim 1 wherein said ringlet has a shape selected from a group consisting of a quatrefoil shape, a pentafoil shape and a hexafoil shape.

7. The ringlet coupler of claim 1 wherein the outer cylindrical wall of the housing has a slot extending there through adapted to permit insertion of the ringlet into the housing.

8. The ringlet coupler of claim 1 wherein the means for securing the ringlet to the housing is a channel defined by a pair of walls.

9. The ringlet coupler of claim 8 wherein the housing has a slot through which the ringlet is inserted into the channel.

10. The ringlet coupler of claim 8 wherein the means for securing the ringlet to the housing comprises a wall and a cap.

11. The ringlet coupler of claim 1 wherein said means for securing the ringlet to the housing comprises an integrally formed ringlet and housing.

12. A ringlet coupler employed in the header of an implantable pulse generator and adapted to make an electrical connection with a contact of a lead pin of a medical lead, said ringlet coupler comprising:
   (a) an electrically conductive housing comprising an outer cylindrical wall defining a first inner surface and a first outer surface, and a pair of cylindrical walls extending inwardly from the inner surface and, together with the inner surface, defining a first channel; and
   (b) an electrically conductive ringlet comprising a band having a second inner surface and a second outer surface, said band fabricated into at least three smoothly curved foils joined together by smoothly curved reduced diameter sections between adjacent foils, wherein said foils are equally spaced about a second channel defined by said reduced diameter sections, wherein each foil has an apex adjacent to the inner surface of the housing within the first channel, wherein the reduced diameter sections are adapted to simultaneously engage a lead pin inserted into the second channel to form an electrical connection and cooperate with the foils and the first channel of the housing to mechanically secure such a lead pin to the electrically conductive ringlet.

13. The ringlet coupler of claim 12 wherein said housing and ringlet are integrally formed.

14. A ringlet coupler employed in the header of an implantable pulse generator and adapted to make an electrical connection with a contact of a lead pin of a medical lead, said ringlet coupler comprising:
   (a) an electrical conductive housing comprising an outer cylindrical wall defining a first inner surface and a first outer surface with a pair of cylindrical walls extending inwardly from the first inner surface of the outer cylindrical wall of the housing;
   (b) an electrically conductive ringlet comprising a band having a second inner surface and a second outer surface, said band fabricated into at least three smoothly curved foils joined together by smoothly curved reduced diameter sections between adjacent foils, wherein said foils are equally spaced about a channel defined by said reduced diameter sections, wherein each foil has an apex adjacent to the inner surface of the housing, a first of the foils having a break at its apex wherein the reduced diameter sections are adapted to simultaneously engage a lead pin inserted into the channel to form an electrical connection and cooperate with the foils and the housing to mechanically secure such a lead pin to the electrically conductive ringlet, said band further comprises a concave area of reduced thickness extending inwardly from the second outer surface at the apex of each of the foils other than the first of the foils, wherein said concave area of reduced thickness extending inwardly from the second outer surface at the apex of said foils is adapted to engage the inner surface of the outer cylindrical wall thereby increasing the area of contact between the ringlet and the outer cylindrical wall of the housing; and
   (c) means for securing the ringlet to the housing.

* * * * *